United States Patent
Glandorf et al.

(12) 
(10) Patent No.: US 6,350,436 B1
(45) Date of Patent: *Feb. 26, 2002

(54) METHOD OF REDUCING STAINING OF STANNOUS IN DENTIFRICE COMPOSITIONS

(75) Inventors: William Michael Glandorf, Mason; Lori Ann Bacca, Lebanon, both of OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/451,420

(22) Filed: Nov. 30, 1999

Related U.S. Application Data

(63) Continuation-in-part of application No. 09/203,216, filed on Nov. 30, 1998, now abandoned, which is a continuation-in-part of application No. 08/754,577, filed on Nov. 21, 1996, now Pat. No. 5,939,052.

(51) Int. Cl.[7] .............................. A61K 7/16; A61K 7/18
(52) U.S. Cl. .............................. 424/52; 424/49; 424/59
(58) Field of Search ..................................... 424/49–88

(56) References Cited

U.S. PATENT DOCUMENTS

| | | | | |
|---|---|---|---|---|
| 2,191,199 A | * | 2/1940 | Hall .............................. | 167/93 |
| 2,946,725 A | * | 7/1960 | Norris et al. ................... | 167/93 |
| 3,004,897 A | * | 10/1961 | Shore .......................... | 167/93 |
| 3,130,002 A | | 4/1964 | Fuchs .......................... | 21/2.7 |
| 4,247,526 A | | 1/1981 | Jarvis et al. ................. | 423/266 |
| 4,340,583 A | * | 7/1982 | Wason ......................... | 424/52 |
| 4,370,314 A | * | 1/1983 | Gaffar ......................... | 424/54 |
| 4,420,312 A | * | 12/1983 | Wason ......................... | 51/308 |
| 4,421,527 A | * | 12/1983 | Wason ......................... | 51/308 |
| 4,452,713 A | | 6/1984 | Small .......................... | 252/99 |
| 4,460,565 A | | 7/1984 | Weststrate et al. ............ | 424/52 |
| 4,515,772 A | | 5/1985 | Parran, Jr. et al. ............ | 424/57 |
| 4,568,540 A | | 2/1986 | Asano et al. .................. | 424/52 |
| 4,627,977 A | | 12/1986 | Gaffar et al. ................. | 424/52 |
| 4,664,906 A | | 5/1987 | Sipos .......................... | 424/49 |
| 4,842,847 A | * | 6/1989 | Amjad ......................... | 424/52 |
| 4,892,725 A | * | 1/1990 | Amjad ......................... | 424/49 |
| 4,913,895 A | | 4/1990 | Miyake et al. ................ | 424/57 |
| 5,000,944 A | * | 3/1991 | Prencipe et al. .............. | 424/57 |
| 5,004,597 A | * | 4/1991 | Majeti et al. ................. | 424/52 |
| 5,096,701 A | | 3/1992 | White, Jr. et al. ............ | 424/52 |
| 5,145,666 A | * | 9/1992 | Lukacovic et al. ............ | 424/52 |
| 5,176,900 A | | 1/1993 | White, Jr. et al. ............ | 424/52 |
| 5,192,532 A | | 3/1993 | Guay et al. ................... | 424/53 |
| 5,213,790 A | * | 5/1993 | Lukacovic et al. ............ | 424/52 |
| 5,281,410 A | * | 1/1994 | Lukacovic et al. ............ | 424/52 |
| 5,320,831 A | | 6/1994 | Majeti et al. ................. | 424/52 |
| 5,320,832 A | * | 6/1994 | Catiis et al. .................. | 424/52 |
| 5,368,844 A | | 11/1994 | Gaffar et al. ................. | 424/49 |
| 5,392,947 A | * | 2/1995 | Gentile ........................ | 220/665 |
| 5,496,540 A | | 3/1996 | Gaffar et al. ................. | 424/49 |
| 5,780,015 A | | 7/1998 | Fisher et al. .................. | 424/52 |
| 5,814,303 A | * | 9/1998 | Williams et al. .............. | 424/57 |
| 5,820,853 A | * | 10/1998 | Glandorf ..................... | 424/52 |
| 5,820,854 A | * | 10/1998 | Glandorf ..................... | 424/52 |
| 5,833,952 A | | 11/1998 | Grigor et al. ................. | 424/49 |
| 5,885,554 A | * | 3/1999 | Michaels et al. .............. | 424/49 |
| 5,891,448 A | * | 4/1999 | Chow et al. ................. | 424/400 |
| 5,902,568 A | * | 5/1999 | Ryles et al. ................... | 424/53 |
| 5,939,052 A | * | 8/1999 | White et al. .................. | 424/52 |

FOREIGN PATENT DOCUMENTS

| | | | | |
|---|---|---|---|---|
| WO | WO 97/46462 | 12/1997 | ............ | A61K/7/16 |

OTHER PUBLICATIONS

Draus, F.J., et al., "Pyrosphosphate and Hexametaphosphate Effects in in Vitro Calculus Formation", Archs Oral Biol., vol. 15 (1970), pp. 893–896.

\* cited by examiner

*Primary Examiner*—Shep K. Rose
(74) *Attorney, Agent, or Firm*—Emelyn DeLeon Hiland; Angela Marie Stone; Betty J. Zea

(57) ABSTRACT

Disclosed are methods for reducing the staining of dentifrice composition containing stannous comprising administering to a subject the dentifrice composition. The dentifrice composition is a dual phase dentifrice and is contained in physically separated compartments of a dentifrice dispenser. The first dentifrice composition comprises an effective amount of one or more linear polyphosphates having an average chain length of about 4 or more and has a total water content of up to about 20%. The second dentifrice composition comprises an effective amount of stannous ions. The molar ratio of polyphosphate anion to stannous ion is from about 0.2:1 to about 5:1 and the efficacy of the stannous ion in the dentifrice is not reduced by the polyphosphate. The dentifrice composition may alternatively be a single phase dentifrice. The single phase dentifrice will comprise an effective amount of one or more linear polyphosphates having an average chain length of about 4 or more and an effective amount of a stannous anion. The single phase dentifrice has a total water content of up to about 20%, the stannous ion is not delivered from stannous fluoride, a molar ratio of polyphosphate anion to stannous ion is from about 0.2:1 to about 5:1, and the efficacy of the stannous ion in the dentifrice is not reduced by the polyphosphate.

21 Claims, No Drawings

METHOD OF REDUCING STAINING OF STANNOUS IN DENTIFRICE COMPOSITIONS

CROSS REFERENCE TO RELATED APPLICATION

This application is a continuation-in-part of application Ser. No. 09/203,216, filed Nov. 30, 1998 now abandoned, which is a continuation-in-part of application Ser. No. 08/754,577, filed Nov. 21, 1996. Now U.S. Pat. 5,939,052.

BACKGROUND OF THE INVENTION

The present invention relates to a method of reducing the staining caused by dentifrice compositions containing stannous. The present inventors have discovered that the use of a polyphosphate will help to reduce the staining that is associated with stannous. It has also been discovered that certain polyphosphates, in particular, linear polyphosphates with average chain lengths of about 4 or more will reduce the staining of the stannous without reducing the efficacy of the stannous.

The term "stannous" as used herein, is defined to mean the stannous that is in a dentifrice. It may refer to the stannous ions that are provided by a stannous salt. Stannous salts which contain stannous ions are commonly known. Stannous has been found to provide antigingivitis and antiplaque benefits. In addition stannous may also help to improve breath and reduce sensitivity. Dentifrices containing stannous are also known to be astringent and to cause staining on a subject's tooth surface. Some previous attempts to reduce the staining of stannous have been successful. However, once the staining was reduced, the efficacy of the stannous was also significantly reduced. For example, when a pyrophosphate, diphosphonate (AHP), and tripolyphosphate are used in a dentifrice with stannous, the efficacy of the stannous is reduced. This reduction in efficacy occurs even if the stannous is in a separate phase from the pyrophosphate, diphosphonate, and tripolyphosphate. One having ordinary skill in the art would assume that a polyphosphate having an average chain length of about 4 or more would behave similarly to the pyrophosphate. The present inventors have found that an unexpected result occurs with the polyphosphate as it reduces the staining but does not significantly reduce the efficacy of the stannous.

To improve consumer acceptance and compliance with the use of dentifrices containing stannous, a method is needed to reduce the amount of staining that occurs on a subjects teeth while still maintaining the efficacy of the stannous.

Therefore, it is an object of the present invention to provide a method of reducing staining of dentifrice composition containing stannous by administering to a subject a stable dentifrice compositions comprising two dentifrice compositions which are contained in physically separated compartments, allowing maximum fluoride and polyphosphate delivery to the oral cavity. The first dentifrice composition comprises a polyphosphate and has a limited total water content while the second composition comprises stannous ions. It is also an object of the present invention to provide a method of reducing staining of dentifrice composition containing stannous by administering to a subject a stable single phase dentifrice composition. The composition will comprise a polyphosphate, a stannous ion delivered from a source other than stannous fluoride, and have a limited total water content.

These and other objects of the present invention will become readily apparent from the detailed description which follows.

All percentages used herein are by weight of the dentifrice composition, unless otherwise specified. The ratios used herein are molar ratios of the overall composition, unless otherwise specified. All measurements are made at 25° C., unless otherwise specified.

SUMMARY OF THE INVENTION

The present invention relates methods for reducing the staining of dentifrice composition containing stannous comprising administering to a subject the dentifrice composition. The dentifrice composition is a dual phase dentifrice and is contained in physically separated compartments of a dentifrice dispenser. The first dentifrice composition comprises an effective amount of one or more linear polyphosphates having an average chain length of about 4 or more and has a total water content of up to about 20%. The second dentifrice composition comprises an effective amount of stannous ions. The molar ratio of polyphosphate anion to stannous ion is from about 0.2:1 to about 5:1 and the efficacy of the stannous ion in the dentifrice is not significantly reduced by the polyphosphate. The dentifrice composition may alternatively be a single phase dentifrice. The single phase dentifrice will comprise an effective amount of one or more linear polyphosphates having an average chain length of about 4 or more and an effective amount of a stannous anion. The single phase dentifrice has a total water content of up to about 20%, the stannous ion is not delivered from stannous fluoride, a molar ratio of polyphosphate anion to stannous ion is from about 0.2:1 to about 5:1, and the efficacy of the stannous ion in the dentifrice is not reduced by the polyphosphate.

DETAILED DESCRIPTION OF THE INVENTION

The dentifrice composition of the present invention may be in the form of a toothpaste or dentifrice. The term "dentifrice", as used herein, means paste, gel, or liquid formulations unless otherwise specified. The dentifrice composition may be in any desired form, such as deep striped, surface striped, multilayered, having the gel surrounding the paste, or any combination thereof.

If a dual phase dentifrice is desired, each dentifrice composition will be contained in a physically separated compartment of a dispenser and dispensed side-by-side. The term "dispenser", as used herein, means any pump, tube, or container suitable for dispensing toothpaste.

The dentifrice composition may be a single phase dentifrice composition or may be a combination of the two or more dentifrice compositions. The dentifrice composition is a product, which in the ordinary course of administration, is not intentionally swallowed for purposes of systemic administration of particular therapeutic agents, but is rather retained in the oral cavity for a time sufficient to contact substantially all of the tooth surfaces and/or oral tissues for purposes of oral activity.

The term "aqueous carrier" as used herein means any safe and effective materials for use in the compositions of the present invention. Such materials include fluoride ion sources, tartar control agents, antibacterial agents, abrasive polishing materials, peroxide sources, alkali metal bicarbonate salts, thickening materials, humectants, water, buffering agents, surfactants, titanium dioxide, flavor system, sweetening agents, coloring agents, and mixtures thereof.

The term "reduced" as used herein means a statistically significant reduction. Therefore, reducing the staining of stannous means that the amount of stain is statistically significantly reduced from a control. Not reducing the efficacy of the stannous means where the efficacy of the stannous is not statistically significantly reduced from a control. A control product containing stannous may be Crest Gum Care.

The present compositions comprise essential components, as well as optional components. The essential and optional components of the compositions of the present invention are described in the following paragraphs.

Stannous Ions

The present invention includes a stannous ion. The stannous ion generally comes from a stannous salt that is added to a dentifrice. Stannous has been found to help in the reduction gingivitis, plaque, sensitivity, and improved breath benefits. The stannous in a dentifrice composition will provide efficacy to a subject using the dentifrice. "Efficacy" is defined as a noticeable amount of reduction in gingivitis as measured by the Plaque Glycolysis Regrowth Model (PGRM). The present inventors have found a way to prevent the efficacy of the stannous from being reduced, while reducing the staining caused by the stannous. Specifically, the efficacy of the stannous is not reduced by the polyphosphate even though the polyphosphate reduces the staining of the stannous. Therefore, the efficacy of the stannous is maintained at a level found in dentifrices containing stannous which are known for reducing gingivitis, such as Crest Gum Care.

The staining of the tooth surface typically caused by stannous is measured on the clinical stain index known as the Lobene stain index. The staining may also be measured on the clinical stain index call the Meckel stain index. The present inventors have found that the stain typically caused by the stannous is reduced by the polyphosphate. As stated, the staining caused by the stannous is reduced but not eliminated. Therefore, the amount of stain resulting from the dentifrice compositions of the present invention is significantly lower than the amount of staining found in typical dentifrices containing stannous, such as Crest Gum Care.

Stannous ions are found in the dentifrice composition in an effective amount. An effective amount is defined as from about 3,000 ppm to about 15,000 ppm. Below 3,000 ppm stannous the efficacy of the stannous is not significant. Preferably, the stannous ion is present in an amount of about 5,000 ppm to about 13,000 ppm and more preferably from about 7,000 ppm to about 10,000 ppm. This is the total amount of stannous ion that is delivered to the tooth surface.

Dentifrices containing stannous salts, particularly stannous fluoride and stannous chloride, are described in U.S. Pat. No. 5,004,597 to Majeti et al., incorporated herein in its entirety. Other descriptions of stannous salt dentifrices are found in U.S. Pat. No. 5,578,293 issued to Prencipe et al. and in U.S. Pat. No. 5,281,410 issued to Lukacovic et al., incorporated herein in its entirety. In addition to the stannous ion source, other ingredients needed to stabilize the stannous may also be included, such as the ingredients described in Majeti et al. and Prencipe et al. Suitable stannous salts include stannous acetate, stannous gluconate, stannous oxalate, stannous sulfate, stannous lactate, stannous tartrate, and combinations thereof. The preferred stannous salts are stannous fluoride and stannous chloride dihydrate. Other stannous salts include stannous acetate. The combined stannous salts will be present in an amount of from about 0.25% to about 11%, by weight of the final composition. Preferably, the stannous salts are present in an amount of from about 0.5 to about 7%, more preferably from about 1% to about 5%, and most preferably from about 1.5% to about 3%.

Polyphosphate Source

The present invention includes a polyphosphate source. Polyphosphates are known to help retard calculus formation. However, it is also known that polyphosphates with an average chain length greater than about 4 will also react with ionic fluoride in oral compositions at ambient temperature and produce monofluorophosphate ions, in addition to altering the pH of the composition. This reaction compromises the efficacy of the oral composition and its ability to provide stable ionic fluoride and polyphosphate to the oral surfaces. It is also known that to have stable polyphosphate, the total water content of the dentifrice composition must be controlled to reduce the hydrolosis of the polyphosphate.

A polyphosphate is generally understood to consist of two or more phosphate molecules arranged primarily in a linear configuration, although some cyclic derivatives may be present. Although pyrophosphates are a polyphosphate, the polyphosphates desired are those having around four or more phosphate molecules. The pyrophosphates are discussed separately. The inorganic polyphosphate salts desired include tetrapolyphosphate and hexametaphosphate, among others. Polyphosphates larger than tetrapolyphosphate usually occur as amorphous glassy materials. Preferred in this invention are the linear "glassy" polyphosphates having the formula:

$$XO(XPO_3)_nX$$

wherein X is sodium or potassium and n averages from about 6 to about 125. Preferred are polyphosphates manufactured by FMC Corporation which are commercially known as Sodaphos (n≈6), Hexaphos (n≈13), and Glass H (n≈21). These polyphosphates may be used alone or in an combination thereof.

The phosphate sources are described in more detail in Kirk & Othmer, *Encyclopedia of Chemical Technology*, Fourth Edition, Volume 18, Wiley-Interscience Publishers (1996), incorporated herein by reference in its entirety, including all references incorporated into Kirk & Othmer. The amount of polyphosphate required is an effective amount which will reduce the staining of the stannous. The effective amount will also reduce tartar. An effective amount of a polyphosphate source will typically be from about 1% to about 20%, preferably from about 2% to about 17%, more preferably from about 4% to about 15%, and most preferably from about 5% to about 13%, by weight of the total dentifrice composition.

For the polyphosphate to have a beneficial effect on reducing the staining of the stannous, the ratio of total moles of polyphosphate anion to total moles of stannous ion should also be controlled. This molar ratio of polyphosphate anion to stannous ion is from about 0.2:1 to about 5:1, preferably from about 0.5:1 to about 3:1, more preferably from about 0.6:1 to about 2:1, and most preferably from about 0.7:1 to about 1:1.

Aqueous Carriers

In preparing the present compositions, it is desirable to add one or more aqueous carriers to the compositions. Such materials are well known in the art and are readily chosen by one skilled in the art based on the physical and aesthetic properties desired for the compositions being prepared. Aqueous carriers typically comprise from about 40% to about 99%, preferably from about 70% to about 98%, and more preferably from about 90% to about 95%, by weight of the dentifrice composition.

Total Water Content

Water employed in the preparation of commercially suitable oral compositions should preferably be of low ion content and free of organic impurities. In the dentifrice composition, water will generally comprise from about 5% to about 70%, and preferably from about 10% to about 50%, by weight of the composition herein. This water content may be in a single phase dentifrice or may be the resulting total water content of a dual phase dentifrice. If the dentifrice composition comprises the polyphosphate having an average chain length of about 4 or more, the dentifrice composition or phase containing the polyphosphate will comprise a lower level of water, generally from about 0% up to about 20% total water. Preferably, the total water content is from about 2% to about 20%, more preferably from about 4% to about 15%, and most preferably from about 5% to about 12%, by weight of the dentifrice composition. The amounts of water include the free water which is added plus that which is introduced with other materials, such as with sorbitol, silica, surfactant solutions, and/or color solutions.

Fluoride Ion Source

The dentifrice compositions of the present invention may incorporate a soluble fluoride source capable of providing free fluoride ions. Soluble fluoride ion sources include sodium fluoride, stannous fluoride, indium fluoride, and sodium monofluorophosphate. Stannous fluoride is the most preferred soluble fluoride ion source. This ingredient may serve as both the stannous ion and fluoride ion source. If a polyphosphate having a chain length of about 4 or more is in the same phase as the fluoride ion source, the preferred fluoride ion source is sodium monofluorophosphate. This is because sodium monofluorophosphate has been found to be more stable than other fluoride sources in the presence of a polyphosphate having an average chain length of about 4 or more. Norris et al., U.S. Pat. No. 2,946,725, issued Jul. 26, 1960, and Widder et al., U.S. Pat. No. 3,678,154 issued Jul. 18, 1972, disclose such fluoride ion sources as well as others. Both patents are incorporated herein by reference in their entirety.

The present compositions may contain a soluble fluoride ion source capable of providing from about 50 ppm to about 3500 ppm, and preferably from about 500 ppm to about 3000 ppm of free fluoride ions. To deliver the desired amount of fluoride ions, stannous fluoride may be present in the total dentifrice composition at an amount of from about 0.1% to about 5%, preferably from about 0.2% to about 1%, and more preferably from about 0.3 to about 0.6%, by weight of the total dentifrice composition.

Buffering Agent

The present compositions may contain a buffering agent. Buffering agents, as used herein, refer to agents that can be used to adjust the pH of the compositions to a range of about pH 3.0 to about pH 10. The phase of the dentifrice containing stannous will typically have a slurry pH of from about 3.0 to about 5.5, preferably from about 3.25 to about 5, and more preferably from about 3.4 to about 4.5. The phase of the dentifrice containing the polyphosphate will typically have a slurry pH of from about 4.0 to about 10, preferably from about 4.5 to about 8, and more preferably from about 5.0 to about 7.0. A dentifrice containing both stannous and polyphosphate in a single phase will typically have a pH of from about 4 to about 7, preferably from about 4.5 to about 6, and more preferably from about 5 to about 5.5.

The buffering agents include alkali metal hydroxides, carbonates, sesquicarbonates, borates, silicates, phosphates, imidazole, and mixtures thereof. Specific buffering agents include monosodium phosphate, trisodium phosphate, sodium benzoate, benzoic acid, sodium hydroxide, potassium hydroxide, alkali metal carbonate salts, sodium carbonate, imidazole, pyrophosphate salts, citric acid, and sodium citrate. Buffering agents are used at a level of from about 0.1% to about 30%, preferably from about 1% to about 10%, and more preferably from about 1.5% to about 3%, by weight of the present composition.

Anticalculus Agents

Optional agents to be used in place of or in combination with the polyphosphate include such materials known to be effective in reducing calcium phosphate mineral deposition related to calculus formation. Agents included are pyrophosphates, tripolyphosphates, synthetic anionic polymers [including polyacrylates and copolymers of maleic anhydride or acid and methyl vinyl ether (e.g., Gantrez), as described, for example, in U.S. Pat. No. 4,627,977, to Gaffar et al., the disclosure of which is incorporated herein by reference in its entirety; as well as, e.g., polyamino propane sulfonic acid (AMPS)], zinc citrate trihydrate, diphosphonates (e.g., EHDP; AHP), polypeptides (such as polyaspartic and polyglutamic acids), and mixtures thereof.

Abrasive Polishing Materials

An abrasive polishing material may also be included in the toothpaste compositions. The abrasive polishing material contemplated for use in the compositions of the present invention can be any material which does not excessively abrade dentin. Typical abrasive polishing materials include silicas including gels and precipitates; aluminas; phosphates including orthophosphates, polymetaphosphates, and pyrophosphates; and mixtures thereof. Specific examples include dicalcium orthophosphate dihydrate, calcium pyrophosphate, tricalcium phosphate, calcium polymetaphosphate, insoluble sodium polymetaphosphate, hydrated alumina, beta calcium pyrophosphate, calcium carbonate, and resinous abrasive materials such as particulate condensation products of urea and formaldehyde, and others such as disclosed by Cooley et al in U.S. Pat. No. 3,070,510, issued Dec. 25, 1962, incorporated herein by reference. Mixtures of abrasives may also be used. If the dentifrice composition or particular phase comprises a polyphosphate having an average chain length of about 4 or more, calcium containing abrasives and alumina are not preferred abrasives. The most preferred abrasive is silica.

Silica dental abrasives of various types are preferred because of their unique benefits of exceptional dental cleaning and polishing performance without unduly abrading tooth enamel or dentine. The silica abrasive polishing materials herein, as well as other abrasives, generally have an average particle size ranging between about 0.1 to about 30 microns, and preferably from about 5 to about 15 microns. The abrasive can be precipitated silica or silica gels such as the silica xerogels described in Pader et al., U.S. Pat. No. 3,538,230, issued Mar. 2, 1970, and DiGiulio, U.S. Pat. No. 3,862,307, issued Jan. 21, 1975, both incorporated herein by reference. Preferred are the silica xerogels marketed under the trade name "Syloid" by the W. R. Grace & Company, Davison Chemical Division. Also preferred are the precipitated silica materials such as those marketed by the J. M. Huber Corporation under the trade name, "Zeodent", particularly the silica carrying the designation "Zeodent 119". The types of silica dental abrasives useful in the toothpastes of the present invention are described in more detail in Wason, U.S. Pat. No. 4,340,583, issued Jul. 29, 1982, incorporated herein by reference. Silica abrasives are also described in Rice, U.S. Pat. Nos. 5,589,160; 5,603,920; 5,651,958; 5,658,553; and 5,716,601; herein incorporated by reference. The abrasive in the toothpaste compositions described herein is generally present at a level of from about 6% to about 70% by weight of the composition. Preferably, toothpastes contain from about 10% to about 50% of abrasive, by weight of the dentifrice composition.

Peroxide Source

The present invention may include a peroxide source in the composition. The peroxide source is selected from the group consisting of hydrogen peroxide, calcium peroxide, urea peroxide, and mixtures thereof. The preferred peroxide source is calcium peroxide. The following amounts represent the amount of peroxide raw material, although the peroxide source may contain ingredients other than the peroxide raw material. The present composition may contain from about 0.01% to about 10%, preferably from about 0.1% to about 5%, more preferably from about 0.2% to about 3%, and most preferably from about 0.3% to about 0.8% of a peroxide source, by weight of the dentifrice composition.

Alkali Metal Bicarbonate Salt

The present invention may also include an alkali metal bicarbonate salt. Alkali metal bicarbonate salts are soluble in water and unless stabilized, tend to release carbon dioxide in an aqueous system. Sodium bicarbonate, also known as baking soda, is the preferred alkali metal bicarbonate salt. The alkali metal bicarbonate salt also functions as a buffering agent. The present composition may contain from about 0.5% to about 50%, preferably from about 0.5% to about 30%, more preferably from about 2% to about 20%, and most preferably from about 5% to about 18% of an alkali metal bicarbonate salt, by weight of the dentifrice composition.

Additional Aqueous Carriers

The present invention compositions in the form of toothpastes, typically contain some thickening material or binders to provide a desirable consistency. Preferred thickening agents are carboxyvinyl polymers, carrageenan, hydroxyethyl cellulose, and water soluble salts of cellulose ethers such as sodium carboxymethylcellulose and sodium hydroxyethyl cellulose. Natural gums such as gum karaya, xanthan gum, gum arabic, and gum tragacanth can also be used. Colloidal magnesium aluminum silicate or finely divided silica can be used as part of the thickening agent to further improve texture. Thickening agents can be used in an of amount from about 0.1% to about 15%, by weight of the dentifrice composition.

Another optional component of the compositions desired herein is a humectant. The humectant serves to keep toothpaste compositions from hardening upon exposure to air and certain humectants can also impart desirable sweetness of flavor to toothpaste compositions. Suitable humectants for use in the invention include glycerin, sorbitol, polyethylene glycol, propylene glycol, xylitol, and other edible polyhydric alcohols. The humectant generally comprises from about 0% to 70%, and preferably from about 15% to 55%, by weight of the composition.

The present compositions may also comprise surfactants, also commonly referred to as sudsing agents. Suitable surfactants are those which are reasonably stable and foam throughout a wide pH range. The surfactant may be anionic, nonionic, amphoteric, zwitterionic, cationic, or mixtures thereof. Anionic surfactants useful herein include the water-soluble salts of alkyl sulfates having from 8 to 20 carbon atoms in the alkyl radical (e.g., sodium alkyl sulfate) and the water-soluble salts of sulfonated monoglycerides of fatty acids having from 8 to 20 carbon atoms. Sodium lauryl sulfate and sodium coconut monoglyceride sulfonates are examples of anionic surfactants of this type. Other suitable anionic surfactants are sarcosinates, such as sodium lauroyl sarcosinate, taurates, sodium lauryl sulfoacetate, sodium lauroyl isethionate, sodium laureth carboxylate, and sodium dodecyl benzenesulfonate. Mixtures of anionic surfactants can also be employed. Many suitable anionic surfactants are disclosed by Agricola et al., U.S. Pat. No. 3,959,458, issued May 25, 1976, incorporated herein in its entirety by reference. Nonionic surfactants which can be used in the compositions of the present invention can be broadly defined as compounds produced by the condensation of alkylene oxide groups (hydrophilic in nature) with an organic hydrophobic compound which may be aliphatic or alkyl-aromatic in nature. Examples of suitable nonionic surfactants include poloxamers (sold under trade name Pluronic), polyoxyethylene, polyoxyethylene sorbitan esters (sold under trade name Tweens), Polyoxyl 40 hydrogenated castor oil, fatty alcohol ethoxylates, polyethylene oxide condensates of alkyl phenols, products derived from the condensation of ethylene oxide with the reaction product of propylene oxide and ethylene diamine, ethylene oxide condensates of aliphatic alcohols, long chain tertiary amine oxides, long chain tertiary phosphine oxides, long chain dialkyl sulfoxides, and mixtures of such materials. The nonionic surfactant poloxamer 407 is one of the most preferred surfactant because the poloxamer has been discovered to help reduce the astringency of the stannous. The amphoteric surfactants useful in the present invention can be broadly described as derivatives of aliphatic secondary and tertiary amines in which the aliphatic radical can be a straight chain or branched and wherein one of the aliphatic substituents contains from about 8 to about 18 carbon atoms and one contains an anionic water-solubilizing group, e.g., carboxylate, sulfonate, sulfate, phosphate, or phosphonate. Other suitable amphoteric surfactants are betaines, specifically cocamidopropyl betaine. Mixtures of amphoteric surfactants can also be employed. Many of these suitable nonionic and amphoteric surfactants are disclosed by Gieske et al., U.S. Pat. No. 4,051,234, issued Sep. 27, 1977, incorporated herein by reference in its entirety. The present composition typically comprises one or more surfactants each at a level of from about 0.25% to about 12%, preferably from about 0.5% to about 8%, and most preferably from about 1% to about 6%, by weight of the composition.

Titanium dioxide may also be added to the present composition. Titanium dioxide is a white powder which adds opacity to the compositions. Titanium dioxide generally comprises from about 0.25% to about 5%, by weight of the composition.

Coloring agents may also be added to the present composition. The coloring agent may be in the form of an aqueous solution, preferably 1% coloring agent in a solution of water. Color solutions generally comprise from about 0.01% to about 5%, by weight of the composition.

A flavor system can also be added to the compositions. Suitable flavoring components include oil of wintergreen, oil of peppermint, oil of spearmint, clove bud oil, menthol, anethole, methyl salicylate, eucalyptol, cassia, 1-menthyl acetate, sage, eugenol, parsley oil, oxanone, alpha-irisone, marjoram, lemon, orange, propenyl guaethol, cinnamon, vanillin, ethyl vanillin, heliotropine, 4-cis-heptenal, diacetyl, methyl-para-tert-butyl phenyl acetate, and mixtures thereof. Coolants may also be part of the flavor system. Preferred coolants in the present compositions are the paramenthan carboxyamide agents such as N-ethyl-p-menthan-3-carboxamide (known commercially as "WS-3") and mixtures thereof. A flavor system is generally used in the compositions at levels of from about 0.001% to about 5%, by weight of the composition.

Sweetening agents can be added to the compositions. These include saccharin, dextrose, sucrose, lactose, xylitol, maltose, levulose, aspartame, sodium cyclamate, D-tryptophan, dihydrochalcones, acesulfame, and mixtures thereof. Various coloring agents may also be incorporated in the present invention. Sweetening agents and coloring agents are generally used in toothpastes at levels of from about 0.005% to about 5%, by weight of the composition.

The present invention may also include other agents, such as antimicrobial agents. Included among such agents are water insoluble non-cationic antimicrobial agents such as halogenated diphenyl ethers, phenolic compounds including phenol and its homologs, mono and poly-alkyl and aromatic halophenols, resorcinol and its derivatives, bisphenolic compounds and halogenated salicylanilides, benzoic esters, and halogenated carbanilides. The water soluble antimicrobials include quaternary ammonium salts and bis-biquanide salts, among others. Triclosan monophosphate is an additional water soluble antimicrobial agent. The quaternary ammonium agents include those in which one or two of the substitutes on the quaternary nitrogen has a carbon chain length (typically alkyl group) from about 8 to about 20, typically from about 10 to about 18 carbon atoms while the remaining substitutes (typically alkyl or benzyl group) have a lower number of carbon atoms, such as from about 1 to about 7 carbon atoms, typically methyl or ethyl groups. Dodecyl trimethyl ammonium bromide, tetradecylpyridinium chloride, domiphen bromide, N-tetradecyl-4-ethyl pyridinium chloride, dodecyl di methyl (2-phenoxyethyl) ammonium bromide, benzyl dimethylstearyl ammonium chloride, cetyl pyridinium chloride, quaternized 5-amino-1,3-bis(2-ethyl-hexyl)-5-methyl hexa hydropyrimidine, benzalkonium chloride, benzethonium chloride and methyl benzethonium chloride are examplary of typical quaternary ammonium antibacterial agents. Other compounds are bis [4-(R-amino)-1-pyridinium]alkanes as disclosed in U.S. Pat. No. 4,206,215, issued Jun. 3, 1980, to Bailey, incorporated herein by reference. Other antimicrobials such as copper bisglycinate, copper glysinate, zinc citrate, and zinc lactate may also be included. Also useful are enzymes, including endoglycosidase, papain, dextranase, mutanase, and mixtures thereof. Such agents are disclosed in U.S. Pat. No. 2,946,725, Jul. 26, 1960, to Norris et al. and in U.S. Pat. No. 4,051,234, Sep. 27, 1977 to Gieske et al., incorporated herein by reference. Specific antimicrobial agents include chlorhexidine, triclosan, triclosan monophosphate, and flavor oils such as thymol. Triclosan and other agents of this type are disclosed in Parran, Jr. et al., U.S. Pat. No. 5,015,466, issued May 14, 1991, and U.S. Pat. No. 4,894,220, Jan. 16, 1990 to Nabi et al., incorporated herein by reference. The water insoluble antimicrobial agents, water soluble agents, and enzymes may be present in either the first or second dentifrice compositions. The quaternary ammonium agents, stannous salts, and substituted guanidines are preferably present in the second dentifrice composition. These agents may be present at levels of from about 0.01% to about 1.5%, by weight of the dentifrice composition.

The dentifrice compositions may be a paste, gel, or any configuration or combination thereof. If a dual phase dentifrice is desired, the first and second dentifrice compositions will be physically separated in a dentifrice dispenser. It is generally preferred that the first dentifrice composition be a paste and the second dentifrice composition be a gel. The dispenser may be a tube, pump, or any other container suitable for dispensing toothpaste. Dual compartment packages suitable for this purpose are described in U.S. Pat. No. 4,528,180, issued Jul. 9, 1985; U.S. Pat. No. 4,687,663, issued Aug. 18, 1987; and U.S. Pat. No. 4,849,213, issued Jul. 18, 1989, all to Shaeffer, all incorporated herein in their entirety. The dispenser will deliver approximately equal amounts of each dentifrice composition through an opening. The compositions may intermix once dispensed. Alternatively, the oral formulation may be delivered from a kit containing two separate dispensers which are used to deliver two dentifrice compositions that are both used simultaneously.

Method of Treatment

The present invention relates to a method of reducing the staining caused by dentifrice composition containing stannous. Each subject may have a different level of staining that occurs. A method of reducing the staining caused by dentifrice compositions containing stannous comprises administering to the subject the claimed dentifrice compositions. The method may also include preparing a dentifrice composition containing stannous and contacting the dentifrice composition with tooth surfaces of a subject. Administering to the subject is defined as having the dentifrice composition contact the tooth surfaces of the subject by brushing with the dentifrice or rinsing with a dentifrice slurry. The subject may be any person or lower animal who uses the dentifrice.

EXAMPLES & METHOD OF MANUFACTURING

The following examples further describe and demonstrate embodiments within the scope of the present invention. These examples are given solely for the purpose of illustration and are not to be construed as limitations of the present invention as many variations thereof are possible without departing from the spirit and scope.

Example I

| First Dentifrice Composition | | Second Dentifrice Composition | |
|---|---|---|---|
| Ingredient | Wt. % | Ingredient | Wt. % |
| Carboxymethycellulose | 0.500 | Sodium Hydroxide[b] | 1.00 |
| Water | 2.768 | Color | 0.300 |
| Flavor | 1.00 | Water | 21.840 |
| Glycerin | 36.432 | Flavor | 1.000 |
| Polyethylene Glycol | 1.500 | Glycerin | 28.992 |
| Propylene Glycol | 8.00 | Sodium Gluconate | 4.160 |
| Sodium Lauryl Sulphate[a] | 4.00 | Stannous Chloride | 3.000 |
| Silica | 28.0 | Silica | 23.000 |
| Benzoic Acid | 0.60 | Sodium Saccharin | 0.30 |
| Sodium Benzoate | 0.600 | Poloxamer | 15.500 |
| Sodium Saccharin | 0.30 | Stannous Fluoride | 0.908 |
| Titanium Dioxide | 1.000 | | |
| Xanthan Gum | 0.30 | | |
| Glass H Polyphosphate | 15.00 | | |

[a]27.9% solution
[b]50% solution

Example II

| First Dentifrice Composition | | Second Dentifrice Composition | |
|---|---|---|---|
| Ingredient | Wt. % | Ingredient | Wt. % |
| Carboxymethycellulose | 0.50 | Sodium Hydroxide[b] | 0.350 |
| Water | 2.768 | Color | 0.300 |
| Flavor | 1.00 | Water | 21.742 |
| Glycerin | 32.200 | Flavor | 1.000 |
| Benzoic Acid | 0.600 | Glycerin | 30.900 |
| Propylene Glycol | 8.000 | Sodium Gluconate | 4.300 |
| Sodium Lauryl Sulphate[a] | 8.00 | Stannous Chloride | 1.700 |
| Silica | 19.232 | Silica | 23.000 |
| Polyoxyl 40 | 2.50 | Sodium Saccharin | 0.30 |
| Polyoxyethylene | 0.500 | Stannous Fluoride | 0.908 |
| Sodium Saccharin | 0.30 | Poloxamer 407 | 15.500 |
| Titanium Dioxide | 1.0 | | |
| Xanthan Gum | 0.30 | | |
| Glass H Polyphosphate | 21.00 | | |
| Polyethylene Glycol | 1.500 | | |
| Sodium Benzolate | 0.600 | | |

[a]27.9% solution
[b]50% solution

Example III

| First Dentifrice Composition | | Second Dentifrice Composition | |
|---|---|---|---|
| Ingredient | Wt. % | Ingredient | Wt. % |
| Carboxymethycellulose | 0.50 | Stannous Chloride | 1.200 |
| Water | 4.500 | Color | 0.300 |
| Flavor | 1.00 | Water | 21.840 |
| Glycerin | 32.200 | Flavor | 1.000 |
| Polyoxyethylene | 0.500 | Glycerin | 33.032 |
| Propylene Glycol | 10.000 | Sodium Gluconate | 2.420 |
| Sodium Lauryl Sulphate[a] | 6.000 | Sodium Hydroxide[b] | 0.500 |
| Silica | 25.000 | Silica | 23.000 |
| Poloxamer 407 | 3.000 | Sodium Saccharin | 0.30 |
| Sodium Benzoate | 0.600 | Poloxamer | 15.500 |
| Sodium Saccharin | 0.300 | Stannous Fluoride | 0.908 |
| Titanium Dioxide | 1.000 | | |
| Xanthan Gum | 0.300 | | |
| Glass H Polyphosphate | 12.00 | | |
| Polyethylene Glycol | 2.500 | | |
| Benzoic Acid | 0.600 | | |

[a] 27.9% solution
[b] 50% solution

The first dentifrice compositions are prepared as follows. Add the water, sodium benzoate and saccharin to a mixing vessel. Disperse carboxymethyl cellulose, xanthan gum and polyoxyethylene in glycerin. Add this glycerin slurry to the mixing vessel, mixing well and heating to at least 40° C. Dissolve the benzoic acid in a mixture of flavor, propylene glycol, poloxamer, sodium lauryl sulphate and polyethylene glycol, then add to the mixing vessel. Next add titanium dioxide and silica. Mix well. Cool the mixing vessel to less than 30° C. and add the polyphosphate. Mix until homogeneous.

The second dentifrice compositions are prepared as follows. Add water, color, and glycerin to the main mix vessel and heat to at least 50° C. Add the sodium gluconate and mix until completely dissolved. Add stannous fluoride and mix until completely dissolved. Add stannous chloride and mix until completely dissolved. Add sodium hydroxide, saccharin and silica and mix well. Add poloxamer and flavor and mix until poloxamer dissolves. Cool batch to less than 30° C.

Example IV

| Ingredient | Wt. % |
|---|---|
| Water | 5.000 |
| Flavor | 1.000 |
| Glycerin | 34.200 |
| Poloxamer 407 | 6.000 |
| Stannous Chloride | 2.000 |
| Sodium Lauryl Sulphate[a] | 6.000 |
| Silica | 23.000 |
| Carboxymethyl cellulose | 0.500 |
| Propylene Glycol | 8.000 |
| Sodium Gluconate | 2.400 |
| Sodium Saccharin | 0.400 |
| Titanium Dioxide | 1.000 |
| Xanthan Gum | 0.300 |
| Qlass H | 8.000 |
| Polyethylene Glycol | 2.000 |
| Polyoxyethylene | 0.200 |

[a] 27.9% solution
[b] 50% solution

Example IV is prepared as follows. Add the water and saccharin to a mixing vessel and heat to at least 50° C. Add the sodium gluconate and mix until completely dissolved. Add stannous chloride and mix until completely dissolved. Add sodium hydroxide and mix until neutralization is complete. Disperse carboxymethyl cellulose, xanthan gum and polyoxyethylene in glycerin. Add this glycerin slurry to the mixing vessel, mixing well. Combine together: flavor, propylene glycol, poloxamer, sodium lauryl sulphate and polyethylene glycol, then add to the mixing vessel. Next add titanium dioxide and silica. Mix well. Cool the mixing vessel to less than 30° C. and add the polyphosphate. Mix until homogeneous.

Example V

| First Dentifrice Composition | | | | |
|---|---|---|---|---|
| Ingredient | Formula A | Formula B | Formula C | Formula D |
| Carboxymethyl cellulose | 0.500 | 0.200 | 0.400 | 0.300 |
| Water | 2.768 | — | — | 1.400 |
| Flavor | 1.000 | 1.300 | 1.200 | 1.100 |
| Glycerin | 36.432 | 45.000 | 42.650 | 39.850 |
| Polyethylene Glycol | 8.000 | — | 4.000 | 6.000 |
| Propylene Glycol | 8.000 | — | — | — |
| Sodium Lauryl Sulfate[a] | 4.000 | 8.000 | 10.000 | 6.000 |
| Silica | 22.000 | 18.500 | 20.000 | 26.000 |
| Benzoic Acid | 0.600 | — | — | 0.300 |
| Sodium Benzoate | 0.600 | — | — | 0.300 |
| Sodium Saccharin | 0.300 | 0.400 | 0.450 | 0.350 |
| Titanium Dioxide | 0.500 | 0.500 | 0.300 | 0.400 |
| Glass H Polyphosphate | 15.000 | 26.000 | 21.000 | 18.000 |
| Xanthan Gum | 0.300 | 0.100 | — | — |

[a] 27.9% solution
[b] 50% solution

| Second Dentifrice Composition | | | | |
|---|---|---|---|---|
| Ingredient | Formula 1 | Formula 2 | Formula 3 | Formula 4 |
| Polyoxyethylene | — | 0.200 | — | — |
| Water | — | 49.158 | 3.750 | 18.100 |
| Flavor | 0.500 | 1.300 | 1.200 | 1.100 |
| FD&C Blue #1 Dye Sol'n | 0.300 | 0.300 | 0.100 | 0.500 |
| Glycerin | 90.485 | 22.000 | 77.310 | 24.240 |
| Polyethylene Glycol | 6.000 | — | — | — |
| PEG 40 Hydrogenated Castor Oil | — | — | — | 6.000 |
| Poloxamer 407 | — | 17.500 | — | — |
| Sodium Lauryl Sulfate[a] | — | 2.500 | 4.500 | 5.400 |
| Silica | — | — | 10.000 | 20.000 |
| Sodium Gluconate | — | 2.760 | — | 0.560 |
| Anhydrous Citric Acid | — | — | — | 0.531 |
| Sodium Citrate | — | — | — | 2.657 |
| Stannous Fluoride | 0.995 | 1.062 | 0.940 | 0.940 |
| Stannous Chloride | 1.420 | 1.320 | — | 0.560 |
| Stannous Sulfate | — | — | 0.700 | — |
| Sodium Hydroxide[b] | — | 0.700 | — | — |
| Sodium Saccharin | — | 0.400 | 0.300 | 0.400 |
| Sodium Fluoride | — | — | — | — |
| Sorbitol | — | — | — | 16.941 |
| Tetrasodium Pyrophosphate | — | — | — | 0.500 |
| Xanthan Gum | 0.300 | 0.800 | 0.600 | 1.100 |
| Hydroxyethyl Cellulose | — | — | 0.600 | 0.500 |

[a] 27.9% solution
[b] 50% solution

In Example V, the first dentifrice compositions are prepared as follows. Add the water, sodium benzoate and saccharin to a mixing vessel. Disperse carboxymethyl cellulose and xanthan gum in glycerin. Add this glycerin slurry to the mixing vessel, mixing well and heating to at least 40° C. Dissolve the benzoic acid in a mixture of flavor, propylene glycol, sodium lauryl sulphate and polyethylene glycol, then add to the mixing vessel. Next add titanium dioxide and silica. Mix well. Cool the mixing vessel to less than 30° C. and add the polyphosphate. Mix until homogeneous.

The second dentifrice compositions are prepared as follows:

For Formula 1, add glycerin, stannous fluoride, and stannous chloride to main mixing vessel and heat, while agitating, to at least 120° F. Once heated, mix until the stannous salts have dissolved. In a separate vessel, mix the polyethylene glycol and xanthan gum, then add this mixture to the main mix tank. Mix under vacuum until homogeneous. Cool the mixture, then add flavor and color. Mix under vacuum until homogeneous.

For Formula 2, add water, color, and glycerin to the main mix vessel and heat to at least 50° C. Add the sodium gluconate and mix throughly. Add stannous fluoride and stannous chloride and mix until completely dissolved. Add the sodium hydroxide, saccharin, polyoxethylene, sodium lauryl sulfate, and xanthan gum and mix well. Add poloxamer and flavor and mix until poloxamer dissolves. Cool batch to less than 30° C.

For Formula 3, add glycerin, xanthan gum and hydroxyethyl cellulose to the main mixing vessel and mix until homogeneous. Add water, stannous fluoride, stannous sulfate and saccharin to main mixing vessel and heat, while agitating, to at least 120° F. Once heated, mix until the stannous salts have dissolved. Cool the mixture, then add silica, sodium lauryl sulfate, flavor and color to the main mixing vessel. Mix under vacuum until homogeneous.

For Formula 4, add water, sorbitol, stannous fluoride, stannous chloride, sodium citrate and citric acid to the main mixing vessel. Heat to 100–160° F. Mix until the stannous salts are dissolved. Add tetrasodium pyrophosphate to the mixture and mix until dissolved. Cool the mixture to room temperature and add saccharin. Mix until dissolved. In a separate vessel, disperse the xanthan gum and hydroxyethyl cellulose into glycerin then add this premix to the main mixing vessel. Mix under vacuum until homogeneous. Add silica, sodium lauryl sulfate, PEG 40 Hydrogenated castor oil, flavor and color to the main mixing vessel. Mix under vacuum until homogeneous.

What is claimed is:

1. A method of reducing staining of a dual-phase dentifrice composition containing stannous for administration to a subject, comprising including in said dentifrice composition contained in physically separated compartments of a dentifrice dispenser:
  a. a first dentifrice composition comprising an effective amount of one or more linear polyphosphates having an average chain length of about 6 to 21, wherein the first dentifrice composition has a total water content of up to about 20% and is essentially free of an ionic fluoride source; and
  b. a second dentifrice composition comprising an effective amount of stannous ions;
wherein a molar ratio of polyphosphate anion to stannous ion is from about 0.2:1 to about 5:1 and the efficacy of the stannous ions in the dentifrice is not reduced by the polyphosphate.

2. A method of reducing staining according to claim 1 wherein the polyphosphate is in an amount of from about 1% to about 20%.

3. A method of reducing staining according to claim 2 wherein the stannous ion is present in an amount of from about 3,000 ppm to about 15,000 ppm.

4. A method of reducing astringency according to claim 1 wherein the polyphosphate is selected from the group consisting of linear "glassy" polyphosphates having the formula $$XO(XPO_3)_nX$$

wherein X is sodium or potassium and n averages from about 6 to about 21.

5. A method of reducing staining according to claim 4 wherein the stannous ion is provided from stannous fluoride.

6. A method of reducing staining according to claim 5 wherein the stannous ion is also provided from stannous chloride dihydrate.

7. A method of reducing staining according to claim 4 wherein the molar ratio of polyphosphate anion to stannous ion is from about 0.5:1 to about 3:1.

8. A method of reducing staining according to claim 4 wherein the first dentifrice composition has a total water content of from about 2% to about 20%.

9. A method of reducing staining according to claim 4 wherein the polyphosphate is Glass H.

10. A method of reducing staining according to claim 9, wherein the dentifrice composition further comprises aqueous carriers comprising a fluoride ion source.

11. A method of reducing staining of a dual-phase dentifrice composition containing stannous for administration to a subject, comprising including in the dentifrice composition a first dentifrice composition contained in a physically separated compartment of a dentifrice dispenser, comprising:
  a. an effective amount of one or more linear polyphosphates having an average chain length of about 6 to 21;
  b. an effective amount of stannous ions;
wherein the first dentifrice composition has a total water content of up to about 20%, a molar ratio of polyphosphate anion to stannous ion is from about 0.2:1 to about 5:1 and is essentially free of an ionic fluoride source, the stannous ion is not delivered from stannous fluoride, and the efficacy of the stannous ions in the dentifrice is not reduced by the polyphosphate.

12. A method of reducing staining according to claim 11 wherein the polyphosphate is in an amount of from about 1% to about 20%.

13. A method of reducing staining according to claim 12 wherein the stannous ion is present in an amount of from about 3,000 ppm to about 15,000 ppm.

14. A method of reducing astringency according to claim 11 wherein the polyphosphate is selected from the group consisting of linear "glassy" polyphosphates having the formula $$XO(XPO_3)_nX$$

wherein X is sodium or potassium and n averages from about 6 to about 21.

15. A method of reducing staining according to claim 14 wherein the molar ratio of polyphosphate anion to stannous ion is from about 0.5:1 to about 3:1.

16. A method of reducing staining according to claim 14 wherein the first dentifrice composition has a total water content of from about 2% water to about 20%.

17. A method of reducing staining according to claim 16 wherein the polyphosphate is Glass H.

18. A method of reducing staining according to claim 15, wherein the dentifrice composition further comprises aqueous carriers comprising a fluoride ion source.

19. A method of reducing staining according to claim 18 wherein the stannous ion is provided from stannous chloride dihydrate.

20. A method of reducing staining according to claim 19 wherein the dentifrice further comprises sodium monofluorophosphate.

21. A method of reducing staining according to claim 11 wherein said dual phase dentifrice composition comprises a second phase dentifrice composition comprising a fluoride ion source.

* * * * *